(12) United States Patent
Lewis et al.

(10) Patent No.: US 11,313,820 B2
(45) Date of Patent: Apr. 26, 2022

(54) METHODS AND SYSTEMS FOR DETERMINING AN INTERNAL PROPERTY OF A FOOD PRODUCT

(71) Applicant: Walmart Apollo, LLC, Bentonville, AR (US)

(72) Inventors: Steven Lewis, Bentonville, AR (US); Matthew Biermann, Fayetteville, AR (US); Suman Pattnaik, Bentonville, AR (US)

(73) Assignee: Walmart Apollo, LLC, Bentonville, AR (US)

(*) Notice: Subject to any disclaimer, the term of this patent is extended or adjusted under 35 U.S.C. 154(b) by 421 days.

(21) Appl. No.: 16/435,800

(22) Filed: Jun. 10, 2019

(65) Prior Publication Data

US 2019/0293583 A1 Sep. 26, 2019

Related U.S. Application Data

(63) Continuation of application No. 15/918,936, filed on Mar. 12, 2018, now Pat. No. 10,359,381.

(Continued)

(51) Int. Cl.
*G01N 27/02* (2006.01)
*G01R 27/16* (2006.01)
*G01N 33/12* (2006.01)

(52) U.S. Cl.
CPC ............. *G01N 27/02* (2013.01); *G01N 33/12* (2013.01); *G01R 27/16* (2013.01)

(58) Field of Classification Search
CPC ........ G01R 27/00; G01R 27/02; G01R 27/16; G01N 27/00; G01N 27/02; G01N 33/02–12
See application file for complete search history.

(56) References Cited

U.S. PATENT DOCUMENTS 4,586,613 A 5/1986 Horii
5,811,680 A 9/1998 Galili et al.
(Continued)

FOREIGN PATENT DOCUMENTS

CN 103278514 A 9/2013
JP 08117694 A * 5/1996
(Continued)

OTHER PUBLICATIONS

First Examination Report issued for GB Patent Application No. 1912753.9 dated Aug. 5, 2021.
(Continued)

*Primary Examiner* — Huy Q Phan
*Assistant Examiner* — David B Frederiksen
(74) *Attorney, Agent, or Firm* — Duane Morris LLP; Manita Rawat (57) ABSTRACT

Systems and methods are provided to determine an internal property of a food product. The system includes one or more analyzing devices, a camera and a central unit in communication with the camera and analyzing device. The analyzing device is configured to analyze an interior region of the food product. The camera is configured to analyze an external property of the food product. The central unit is configured to determine the internal property of the food product based on feedback provided by the analyzing device and the camera.

20 Claims, 6 Drawing Sheets

Related U.S. Application Data (60) Provisional application No. 62/470,005, filed on Mar. 10, 2017.

(56) References Cited

U.S. PATENT DOCUMENTS

| | | | |
|---|---|---|---|
| 6,240,766 | B1 | 6/2001 | Cawley |
| 6,242,714 | B1 * | 6/2001 | Narumiya ............... G01K 7/343 219/385 |
| 6,587,575 | B1 | 7/2003 | Windham et al. |
| 6,784,405 | B2 | 8/2004 | Flagstaff et al. |
| 6,875,958 | B2 | 4/2005 | Soavi et al. |
| 6,998,559 | B2 | 2/2006 | De Baerdemaeker et al. |
| 8,457,904 | B2 | 6/2013 | Burke et al. |
| 9,474,404 | B2 | 10/2016 | Jeong et al. |
| 2005/0019454 | A1 * | 1/2005 | Kennedy ................... B07C 5/34 426/231 |
| 2006/0218057 | A1 | 9/2006 | Fitzpatrick et al. |
| 2009/0274804 | A1 | 11/2009 | Wilson et al. |
| 2010/0179884 | A1 * | 7/2010 | Glaser ................ G06Q 30/0601 705/26.1 |
| 2012/0237644 | A1 | 9/2012 | Luckhardt et al. |
| 2013/0112895 | A1 * | 5/2013 | Birlouez-Aragon ... G01N 33/02 250/459.1 |
| 2014/0050824 | A1 | 2/2014 | Rapoport |
| 2014/0267684 | A1 * | 9/2014 | Nelson .................. G01N 21/94 348/89 |
| 2014/0331796 | A1 * | 11/2014 | Lee ........................ G01N 22/00 73/866 |
| 2015/0036138 | A1 | 2/2015 | Watson et al. |
| 2015/0216442 | A1 | 8/2015 | Lavy et al. |
| 2016/0091434 | A1 * | 3/2016 | Fagan .................... G01N 21/85 356/318 |
| 2016/0140870 | A1 | 5/2016 | Connor |
| 2016/0260352 | A1 | 9/2016 | Ortiz |
| 2016/0350715 | A1 * | 12/2016 | Minvielle .............. G01N 33/02 |
| 2018/0113083 | A1 * | 4/2018 | Van Dael ............. G01N 33/025 |

FOREIGN PATENT DOCUMENTS

| | | |
|---|---|---|
| JP | 08117694 A | 5/1996 |
| JP | H8-117694 A | 5/1996 |

OTHER PUBLICATIONS

Digi International Inc., "Introducing Digi Honeycomb: A Food-Grade Temperature Monitoring Solution"; https://www.youtube.com/watch?v=dqwbOno4Ge0; accessed Mar. 9, 2018.

International Search Report and Written Opinion dated May 23, 2018 in corresponding International Application No. PCT/US18/22058 (11 pp).

Zheng, C. et al. "Recent developments and applications of image features for food quality evaluation and inspection—a review." Trends in Food Science & Technology, 2006, vol. 17 (pp. 642-655).

* cited by examiner

METHODS AND SYSTEMS FOR DETERMINING AN INTERNAL PROPERTY OF A FOOD PRODUCT

CROSS REFERENCE TO RELATED APPLICATIONS

This application is a Continuation of U.S. patent application Ser. No. 15/918,936, filed on Mar. 12, 2018, which claims the benefit of priority to U.S. Provisional Application No. 62/470,005, filed on Mar. 10, 2017, the entire contents of which are hereby incorporated by reference.

FIELD OF THE INVENTION

The present invention relates to systems and methods for determining internal properties of a food product, and more particularly, to more accurately determine such internal properties that are not readily detectable by the naked eye.

BACKGROUND OF THE INVENTION

Over time, various methodologies have been developed to roughly determine internal properties of food products. For example, to determine the ripeness of cantaloupes, individuals attempt to ensure that they weigh more than their appearance and are of appropriate smell. Along these lines, to determine the ripeness of watermelons, individuals utilize a wide range of different methodologies, such as inspecting their size, hollowness, smell and appearance.

Moreover, the internal properties of some food products may not be able to be readily determined. For instance, to determine the freshness of fish, individuals look to the pleasantness of the smell, the moistness of the gills and fins, the appearance of the eyes, etc. Along these lines, to determine the marbling of meat, individuals merely look at its external appearance.

Accordingly, systems and methods are needed to allow individuals to accurately and readily determine one or more internal properties of food products. Moreover, systems and methods are needed to allow individuals to accurately and readily do so across a wide range of food products. The present invention provides such systems and methods.

BRIEF SUMMARY OF THE INVENTION

In one aspect of the invention, a system for determining an internal property of a food product is provided, including one or more analyzing devices, a camera and a central unit. The analyzing device is configured to analyze an interior region of the food product. The camera is configured to analyze an exterior property of the food product. The central unit is in communication with the camera and the device, and it is configured to determine the internal property of the food product based on feedback of the analyzing device and the camera.

The analyzing device can comprise a probe having an elongated bar. The elongated bar can have two electrodes. The central unit can be configured to apply a current to the first and the second electrode to measure the impedance between the electrodes. The analyzing device can also comprise an ultrasound device capable of providing an image of the interior portion of the food product.

The system can also comprise at least one of a scale, a server and a display, wherein each of these components can be in communication with the central unit. The scale can be configured to determine a weight of the food product, and the central unit can be configured to determine an identity of the food product based on the weight of the food product. Moreover, the server can be configured to store a plurality of internal and external properties of the food product, and the central unit can be configured to determine the internal property of the food product by comparing the feedback of the analyzing device and the camera to the internal and external properties of the food product stored in the server. Furthermore, the display can be configured to present information pertaining to the food product to the user.

In another aspect of the invention, a system for determining an internal property of a food product is provided, including one or more analyzing devices comprising a probe having an elongated bar configured to be inserted into the food product, wherein the elongated bar comprises a first and second electrode. The system also includes a scale configured to measure a weight of the food product, a camera configured to analyze an external property of the food product and a central unit in communication with each of these components. The central unit is configured to apply a current to the electrodes and measure an impedance across them. Moreover, the central unit is further configured to determine the internal property of the food product based on the impedance of the portion of the interior region of the food product, the weight of the food product and the external property of the food product.

The system can also comprise a server and a display, wherein each of these components can be in communication with the central unit. The server can be configured to store a plurality of internal and external properties of the food product. The central unit can determine the internal property of the food product by comparing the impedance of the portion of the interior region of the food product and the external property of the food product to the plurality of internal and external properties of the food product stored in the server. The display can be configured to present information pertaining to the food product to the user, wherein each of these components are in communication with the central unit.

In another aspect of the invention, a method for determining an internal property of a food product is provided. The method can include the steps of capturing an image of the food product to analyze an external property of the food product via a camera, analyzing an interior region of the food product via one or more analyzing devices, and determining an internal property of the food product based on feedback of the analyzing device and the camera.

BRIEF DESCRIPTION OF THE DRAWINGS

The features and advantages of the invention will be apparent from the following drawings wherein like reference numbers generally indicate identical, functionally similar, and/or structurally similar elements.

In the drawings.

DETAILED DESCRIPTION OF THE PRESENT INVENTION

Reference will now be made in detail to various embodiments of the present invention, examples of which are illustrated in the accompanying drawings. It is to be understood that the figures and descriptions of the present invention included herein illustrate and describe elements that are of particular relevance to the present invention. It is also important to note that any reference in the specification to "one embodiment," "an embodiment" or "an alternative embodiment" means that a particular feature, structure or characteristic described in connection with the embodiment is included in at least one embodiment of the invention. As such, the recitation of "in one embodiment" and the like throughout the specification do not necessarily refer to the same embodiment.

The systems and methods disclosed herein are intended to determine one or more internal and/or external properties of a food product. The internal properties of the food product can be based on detected external properties of the food products. As such, the systems and methods can be implemented in a retail setting, but are not limited to use in a retail setting. Alternatively, the systems and methods disclosed herein may be utilized for personal home use, or they may be utilized in the production or management of the food products by a food supplier or grocery retailer.

Food product as used herein refers to any substance that can be used as food. For example, the food product can be meat, seafood, fish, fruit, vegetables or bread. More specifically, the food product can be a steak, salmon, strawberry, cantaloupe, watermelon, etc.

External property as used herein refers to any external characteristic related to the food product. For example, the external property can be a color, a shape, a size and a texture of the food product.

Internal property as used herein refers to any internal characteristic related to the food product. For example, the internal property can be protein content, fat content, seed content, water content, degree of ripeness, etc. More specifically, the internal property can be grams of protein, grams of fat, amount of seeds relative to the weight of food product, percentage of water content, degree of ripeness compared to average food product, estimated shelf life, etc.

Along these lines, the internal and/or external properties of each food product may not be identical, and they may be dependent on the identity of the food product. As such, each food product may have one or more internal and/or external properties unique to its identity. For example, a strawberry may have one or more internal and external properties unique to itself, and those properties may be different than those of poultry. Along these lines, the internal and/or external properties of each food product may be based on whether the food is organic or non-organic. For example, where the food product is organic, the internal property can be the amount of pesticides, fertilizers, chemical preservatives and monosodium glutamate (MSG) in the food product.

Retail setting as used herein refers to any online or brick-and-mortar outlet selling one or more food products to the public including, but not limited to, grocery stores, department stores, supermarkets, hypermarkets, warehouse stores, specialty stores, retail store, etc.

Figure 1:
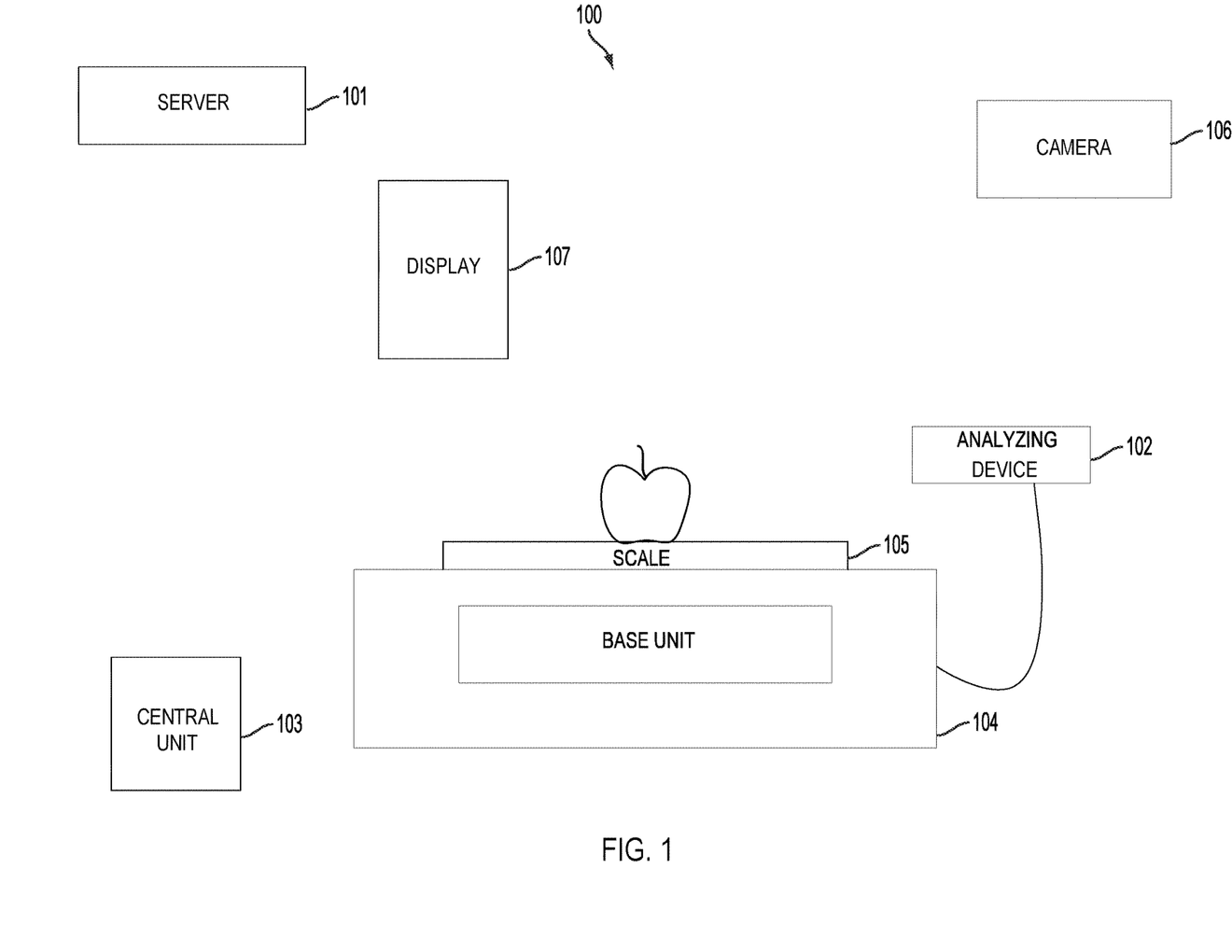
FIG. 1 illustrates an exemplary system for determining an internal property food product in accordance with the principals of the present invention.

Referring now to the figures, various exemplary embodiments of systems for determining an internal property of a food product and methods thereof will be described. Referring to FIG. 1, a system 100 for determining an internal property of a food product can be provided. The system can be for use by a manufacturer, seller, purchaser or the like. As shown, the system 100 can include one or more of a server 101, an analyzing device 102, a central unit 103, a base unit 104, a scale 105, a camera 106, and a display 107. Each of these components will be discussed at length below.

The Base Unit

As shown, the base unit 104 can comprise a display capable of providing one or more instructions for operation of the system to the user, as will be described below. The base unit 104 can also comprise the scale 105. Specifically, the base unit 104 can have a place for the scale 105 to reside thereon. Concavely, although not illustrated, the scale 105 can be integrated into the unit. Moreover, although not illustrated, the base unit 104 may be a standalone unit merely serving as a place for the user to place the food product.

The Scale

The scale 105 is configured to determine a weight of the food product. The scale 105 can be in communication with the central unit 103 and configured to transmit the weight of the food product to the central unit 103. As discussed above, and as illustrated in FIG. 1, the scale 105 can be a part of the base unit 104. Alternatively, the scale 105 can be a standalone unit.

The Camera

As illustrated in FIG. 1, the camera 106 can be wirelessly connected to the central unit 103. Alternatively, although not illustrated, the camera 106 may have a wired connection to the base unit 104 and/or analyzing device 102 comprising the central unit 103 to be in electrical communication therewith. Moreover, the camera 106 can be configured to take one or more pictures of an exterior region of the food product. The camera 106 may be configured to automatically take the picture of the food product upon placement of the food product onto the base unit 104. Alternatively, the camera 106 can be configured to take the picture of the food product upon indication by the user. Along these lines, the camera 106 may be configured to take the picture prior to the device analyzing the interior region of the food product. Alternatively, the camera 106 may be configured to take the picture after receiving information from analyzing the interior region of the device.

The Analyzing Device

The analyzing device 102 can be configured to analyze the interior region of the food product any number of ways. The analyzing device 102 can also comprise a wire outwardly extending from an end of the handle opposite of the first end to the base unit 104. The wire can be for the device to electrically communicate with the base unit 104, or it can be for maintaining physical connection to the base unit 104. Alternatively, although not illustrated, the device can be in wireless communication with the base unit 104.

Figure 2:
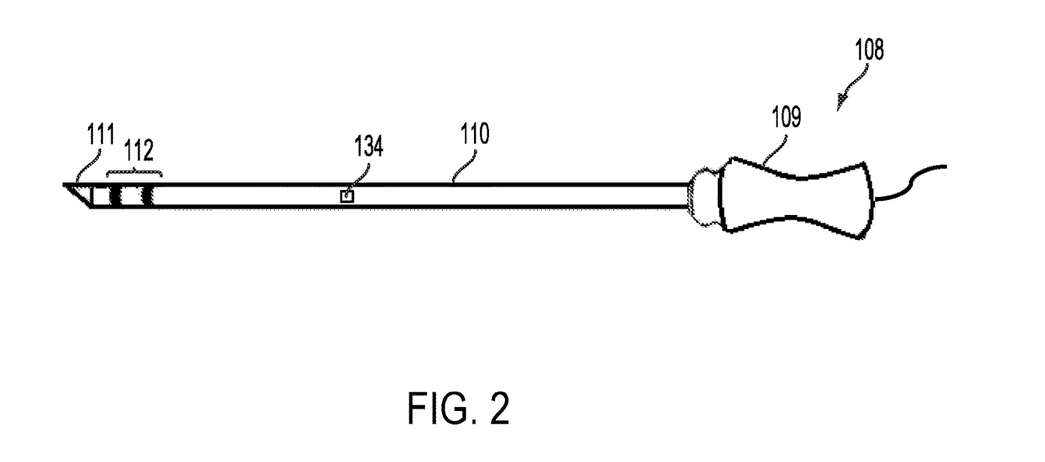
FIGS. 2-4 illustrate exemplary devices for analyzing an internal portion of a food product in accordance with the principals of the present invention.
Figure 3:
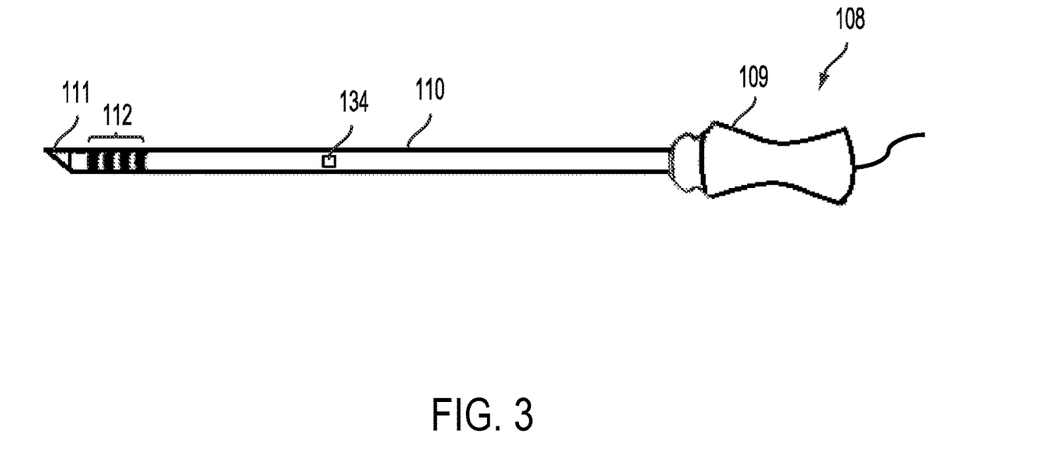

In some embodiments, as illustrated in FIGS. 2 and 3, the analyzing device 102 (illustrated in FIG. 1) can be a probe 108. The probe 108 can comprise a handle 109 for the user to grab, an elongated structure 110 attached to and extending outwardly from a first end of the handle 109, and a sharp tip 111 attached to and outwardly extending an end of the elongated structure opposite from the handle 109. The elongated structure 110 can further comprise a sensor 134 configured to send a signal to the user to indicate that the user has inserted a sufficient portion of the elongated structure into the food product. Moreover, the elongated structure 110 can be of a size and strength to allow it to be easily inserted into the food product without significant difficulty by the user, and to not cause a hole in the food product noticeable by the naked eye.

Furthermore, the elongated structure 110 of the probe 108 may comprise one or more electrodes 112 configured to determine an impedance of an interior region of the food product. For instance, as illustrated in FIG. 2, the probe 108 can comprise an elongated structure 110 having two electrodes 112 spaced from each other at an end of the probe 108 to be inserted into the food product. Alternatively, as illustrated in FIG. 3, the elongated structure 110 may have multiple pairs of electrodes 112 utilized to measure an impedance between various interior regions of the food product. In each of these embodiments, the central unit 103 (illustrated in FIG. 1) can be configured to transmit an electrical signal to the electrode(s) of each elongated structure, and to measure an impedance of an interior region between each pair of electrodes 112.

Figure 4:
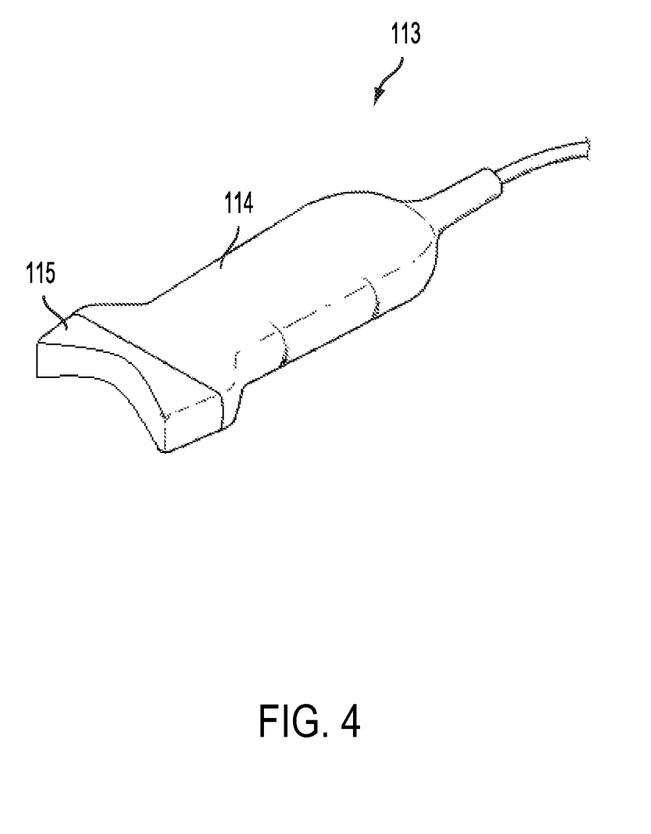

In an alternative embodiment, as shown in FIG. 4, the analyzing device 102 (illustrated in FIG. 1) can be an ultrasound device 113. The ultrasound device 113 can have a first end 114 and a second end 115. The first end 114 can comprise a handle 190 for the user to grab. The second end 115 can be configured to direct frequencies to the food product. As such, as illustrated, the second end 115 can be arc shaped.

Upon receipt of an electrical signal from the central device, the ultrasound device 113 sends sound waves having low frequencies for a predetermined amount of time to the food product. Preferably, the frequency is in the range of 100 kHz and 1 W/cm². The sounds echoes are recorded by the central device and capable of being transformed to an image of the inside of the food product. As such, the ultrasound device 113 is not intrusive and may be considered preferable to the probe 108 (illustrated in FIGS. 2 and 3).

In yet a further embodiment, the probe 108 and ultrasound device 113 can both be used to determine the internal properties of the food product. They can be used in conjunction with each other to provide a more accurate representation of the internal properties of the food product.

The Display

Referring back to FIG. 1, as stated above, the display 107 can be configured to present one or more instructions to the user. For example, the display 107 provides to the user one or more of the following instructions—(i) placement of the food product on the base unit and/or scale, (ii) how to inject the probe into the food product, and (iii) how to utilize the ultrasound device to determine the internal property.

Along these lines, prior to analyzing the internal property of the food product, the display 107 can be configured to present one or more questions to assist in determining the internal property. For example, the display 107 can request that the user enter the type of food product (i.e., steak, fish, watermelon, cantaloupe, etc.). Based on the food type, the display 107 can provide a list of one or more internal properties that may be determined for the user to select.

Alternatively, the system may not require any information relating to the food product that will be analyzed. The server 101 may automatically determine the food type and related internal properties through utilization of the analyzing device 102, and thereafter, present them to the user via the display 107. For example, after injecting the probe into a watermelon and/or swiping the ultrasound device across the watermelon, the system may automatically determine the food product is a watermelon and internal properties relating thereto include seed content, percentage of water, percentage of meat, degree of ripeness, age, shelf life, etc. Subsequently, the display 107 can present the identity of the food product and one or more of the internal properties to the user.

Moreover, the display 107 can also be configured to provide an image of the food product. The image can be two- or three-dimensional, and it can also include an interior and/or exterior of the food product. Along these lines, the image can provide a virtual representation of the internal properties of the food product. Moreover, the image can provide augmented reality of the internal and exterior of the food product. As such, the display 107 can be configured to provide an image presenting the composition, structure and physical state of the food product The Central Unit The central unit 103 can be integrated into the base unit 104 or the analyzing device 102. Alternatively, the central unit 103 can be a standalone unit. The central unit 103 can be configured to receive information from one or more of the scale 105, the camera 106, and/or the analyzing device 102. Upon receipt of the information, the central unit 103 can be configured to send this information to the server 101 for determination of the internal and/or external properties of the food product. Thereafter, the central unit can be configured to receive results from the server 101. Alternatively, the central unit 103 can be configured to determine the internal and/or external properties of the food product without sending the received information to the server 101.

The Server

The server 101 can be configured to store one or more internal and external properties relating to each of one or more food products. The internal and/or external properties of each food product may not be identical, and they may be based on the identity of the food product by the camera. As such, each food product may have one or more internal and external properties unique to its identity. For example, a strawberry may have one or more internal and external properties unique to itself, and those properties may be different than those of poultry. Along these lines, the internal and/or external properties of each food product may be based on whether the food is organic or non-organic.

The server 101 can be solely in communication with the central unit 103 which receives information from the various components of the system. Alternatively, the server 101 can be communication with one or more of the analyzing device 102, central unit 103, base unit 104, scale 105, camera 106 and display 107.

According to an embodiment, the server 101 can determine the identity of the food product based on information received by the camera 106. For example, the server 101 can be configured to determine an identity of the food product based on one or more external properties detected in an image taken by the camera 106. Along these lines, the scale 105 can assist the server 101 in determining the identity of the food product. For example, the server 101 can limit the number of possibilities based on the weight of the food product and, thereafter, determine the identity of the food product from the remaining possibilities.

Furthermore, the server 101 can determine one or more internal properties of the food product based on the analyzing device 102. For example, where the analyzing device 102 comprises a probe having an elongated structure bearing two electrodes, the server 101 can determine one or more internal properties based on an impedance across an interior region of the food product between the electrodes. Alternatively, where the analyzing device 102 comprises an ultrasound device, the server 101 can determine one or more internal properties based on an image of an interior portion of the food product. Yet again, where the analyzing device 102 comprises a probe and an ultrasound device. In such an embodiment, the server 101 can determine one or more internal properties based on the impedance across the electrodes and the image of the interior portion of the food product.

Figure 5:
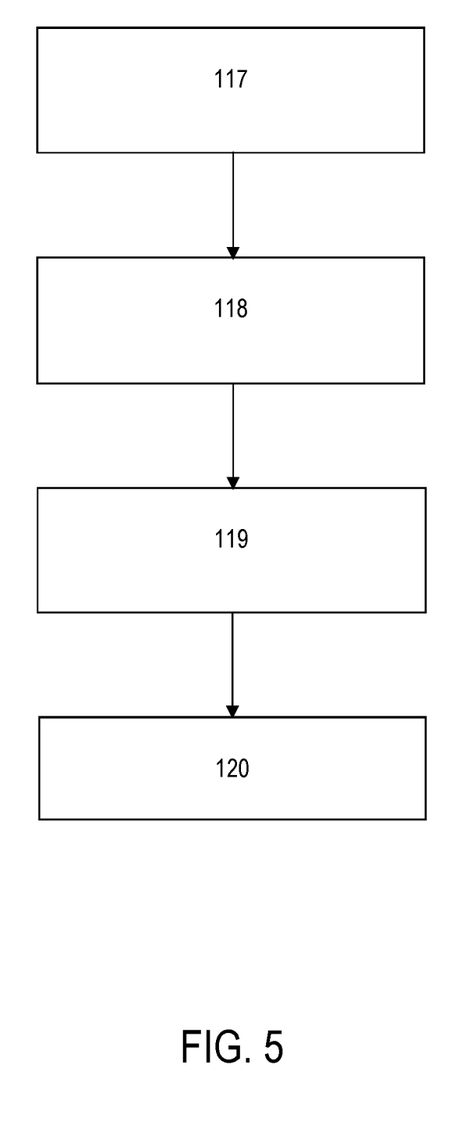
FIG. 5 illustrates an exemplary method for determining an internal property of a food product in accordance with the principals of the present invention.

Referring now to FIG. 5, an exemplary method for determining an internal property of a food product of determining an internal property of a food product is presented that can be performed in accordance with one or more embodiments of the present invention. First, at block 117, a camera captures an image of a food product to analyze an external property of the food product. As described above, a scale may also determine a weight of the food product. Thereafter, at block 118, one or more analyzing devices analyze an interior region of the food product. Subsequently, at block 119, an internal property of the food product is determined based on feedback of the analyzing device and the camera. Lastly, at block 120, the internal property of the food product is displayed via a display. Each of these steps can be processed in accordance with embodiments of the invention as described above.

Regression analysis may be used to determine the properties of the item when it is purchased by a customer. These properties may be correlated with a number of the same items sold over time in order to identify those properties of the item that are present when customers purchase the item. For example, customers may often purchase a watermelon when in makes a solid sound when "thumped" with a finger. The analysis tracks and records this type of data gathered as described above. Regression analysis performed using the various parameters and physical properties of the item for a number of customer transactions provides a model expression to predict the quality of food products and recommend the optimal time of receipt and quality.

In an example, the regression analysis may have one or more of the following inputs:

1) Duration, a particular food product (e.g., a fruit like water melon or cantaloupe or apple etc.) have spent in the store from the time of receipt.
2) Purchase time from the time of receipt
3) Overall color at the point of receipt
4) Overall frequency of response sound to ultra violet emission (Mimicking the finger "thump" process many consumers do on watermelon)
5) Overall Weight
6) Processing type (Natural vs manmade, e.g. in a case of similar to bananas)
7) Optional Packaging, Route to store and placement in store parameters Additional properties of the item may also be included, or substituted in place of the above.

Once identified, the qualities customers like to see in the item may be used to determine when items currently in the store may be sold. The inventory system may predict the sales rate for the item, and determine when additional items should be ordered in order to maintain ideal inventory levels. For example, a batch of items, watermelons, may be received at a store. A sample number of the items may be analyzed. If the sample indicates that the watermelons are at or near the optimum selling point, the inventory system can automatically order new inventory. If the sample indicates that the items have yet to reach the selling point, the inventory system is freed up to process other tasks, improving speed and efficiency of the system. Items or a subset of the items may be analyzed when received and at other points, for example, after being on a shelf for predetermined period of time. Inventory and order decisions may be automated based on the regression analysis and model.

Figure 6:
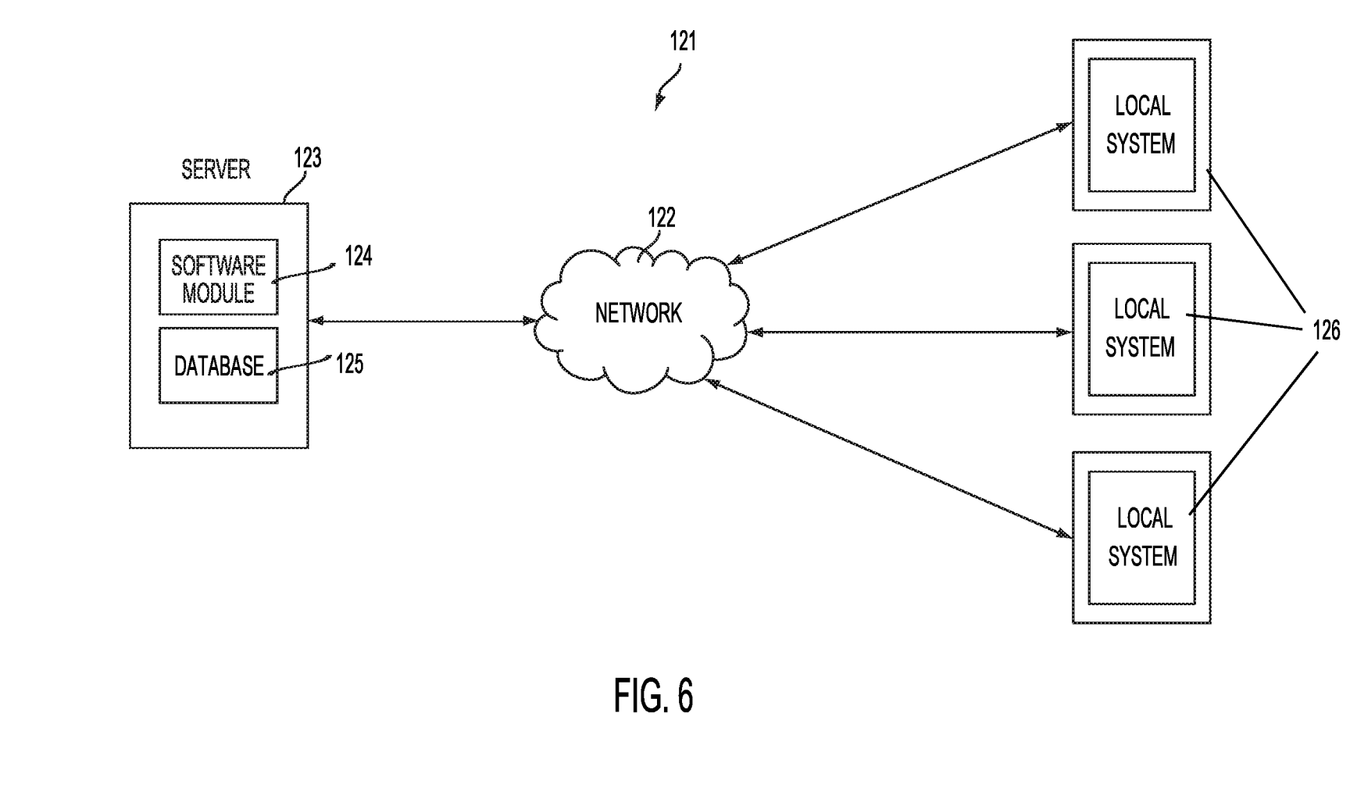
FIG. 6 illustrates an exemplary system for determining an internal property of a food product at multiple local units in accordance with the principals of the present invention.

Referring now to FIG. 6, a diagram of an exemplary system 121 is shown that may be utilized in accordance with one or more embodiments of the present invention as discussed above. System 121 can include a network 122, server 123, software module 124, database 125 and one or more local systems 126. The local system 126 can comprise one or more of a server, an analyzing device, a camera, a base unit, a scale, a central device and a display as described above. The local system 126 and the server 123 can be coupled to a network 122 and configured to send and/or receive data to the network 122. According to an embodiment, the components of each of the local systems 126 can communicate with the server 123 over the network 122 to determine the ripeness of a food product.

Network 122 can provide network access, data transport and other services to the devices coupled to it in order to send/receive data from any number of user devices, as explained above. In general, network 122 can include and implement any commonly defined network architectures including those defined by standard bodies, such as the Global System for Mobile Communication (GSM) Association, the Internet Engineering Task Force (IETF), and the Worldwide Interoperability for Microwave Access (WiMAX) forum.

Server 123 can also be any type of communication device coupled to network 122, including but not limited to, a personal computer, a server computer, a series of server computers, a mini computer, and a mainframe computer, or combinations thereof. Server 123 can be a web server (or a series of servers) running a network operating system. Server 123 can be used for and/or provide cloud and/or network central.

Database 125 can be any type of database, including a database managed by a database management system (DBMS). A DBMS is typically implemented as an engine that controls organization, storage, management, and retrieval of data in a database. DBMSs frequently provide the ability to query, backup and replicate, enforce rules, provide security, do computation, perform change and access logging, and automate optimization.

Software module 124 can be a module that is configured to send, process, and receive information at server 123. Software module 124 can provide another mechanism for sending and receiving data at server 123 besides handling requests through web server functionalities.

Although software module 124 can be described in relation to server 123, software module 124 can reside on any other device. Further, the functionality of software module 124 can be duplicated on, distributed across, and/or performed by one or more other devices, either in whole or in part.

Figure 7:
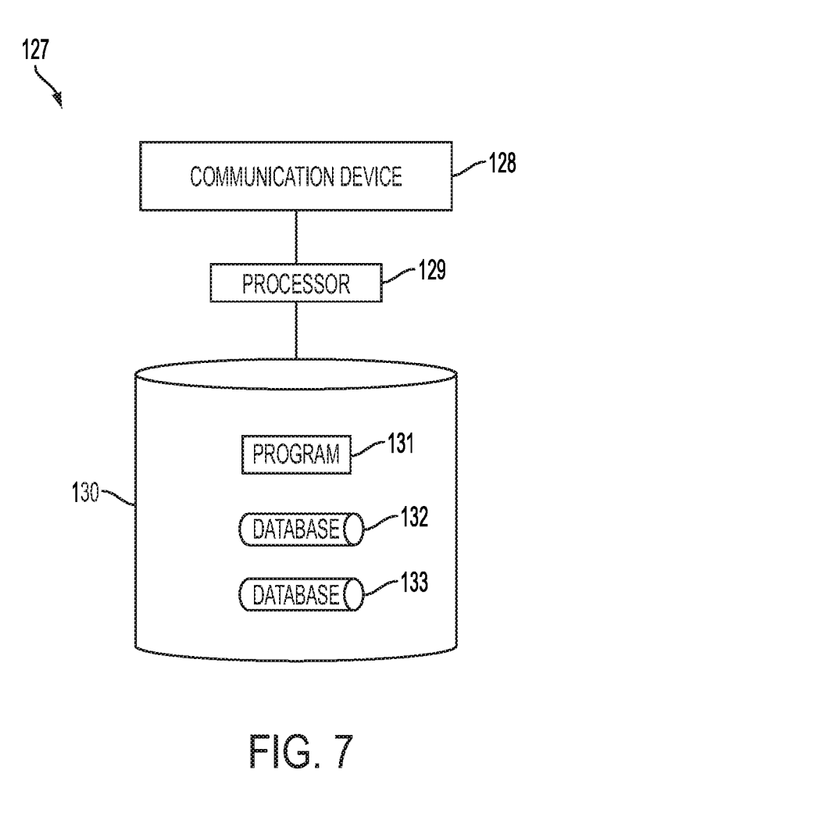
FIG. 7 illustrates an exemplary controller device in accordance with the principals of the present invention.

Referring now to FIG. 7, a schematic diagram of an exemplary central unit 127 is illustrated in accordance with one or more embodiments of the present invention as discussed above. The exemplary central unit 127 includes a processor 129, a communication device 128 and a data storage or memory component 130. The processor 129 is in communication with both the communication device 128 and the memory component 130. The communication device 128 may be configured to communicate information via a communication channel, wired or wireless, to electronically transmit and receive digital data related to the functions discussed herein. The communication device 128 may also be used to communicate, for example, with one or more human readable display devices. The memory component 130 may comprise any appropriate information memory component, including combinations of magnetic memory components (e.g., magnetic tape, radio frequency tags, and hard disk drives), optical memory components, computer readable media, and/or semiconductor memory devices. The memory component 130 may store the program 131 for controlling the processor 129. The processor 129 performs instructions of the program 131, and thereby operates in accordance with the present invention. The memory component 130 may also store and send all or some of the information sent to the processor 129 in one or more databases 132 and 133.

Communication device 128 may include an input device including any mechanism or combination of mechanisms that permit an operator to input information to communication device 128. Communication device 128 may also include an output device that can include any mechanism or combination of mechanisms that outputs information to the operator.

While various exemplary embodiments have been described above, it should be understood that they have been presented by way of example only, and not limitation. Thus, the breadth and scope of the present disclosure should not be limited by any of the above-described exemplary embodiments.

Although the foregoing description is directed to the preferred embodiments of the invention, it is noted that other variations and modifications will be apparent to those skilled in the art, and can be made without departing from the spirit or scope of the invention. Moreover, features described in connection with one embodiment of the invention can be used in conjunction with other embodiments, even if not explicitly stated above.

Use of language such as "at least one of X, Y, and Z," "at least one of X, Y, or Z," "at least one or more of X, Y, and Z," "at least one or more of X, Y, or Z," "at least one or more of X, Y, and/or Z," or "at least one of X, Y, and/or Z," are intended to be inclusive of both a single item (e.g., just X, or just Y, or just Z) and multiple items (e.g., {X and Y}, {X and Z}, {Y and Z}, or {X, Y, and Z}). The phrase "at least one of" and similar phrases are not intended to convey a requirement that each possible item must be present, although each possible item may be present.

The various embodiments described above are provided by way of illustration only and should not be construed to limit the scope of the disclosure. Various modifications and changes may be made to the principles described herein without following the example embodiments and applications illustrated and described herein, and without departing from the spirit and scope of the disclosure.

We claim:

1. A method comprising:
capturing an image of a food product;
analyzing an interior region of the food product via one or more analyzing devices;
based on the image and the analyzing of the interior region, generating, by a processor, a first dataset characterizing (i) at least one internal property of the food product, and (ii) an identity of the food product;
based at least on the first dataset, generating by the processor, a second dataset characterizing a predicted quality of the food product and a recommended optimal time of receipt and quality of the food product by applying a regression analysis on at least the first dataset; and
modifying, by the processor, a purchase order for additional quantities of the food product based on the second dataset.

2. The method of claim 1, wherein the at least one internal property comprises an overall frequency response to ultra violet emission.

3. The method of claim 1, wherein the regression analysis further uses, as inputs, a time of receipt of the food product and a purchase time from the time of receipt.

4. The method of claim 1, wherein the one or more analyzing devices comprises an ultrasound device, and wherein the analyzing of the interior region via the ultrasound device generates an ultrasound.

5. The method of claim 1, wherein the one or more analyzing devices comprises a probe, the probe having at least two electrodes; and
wherein the analyzing of the interior region comprises inserting the probe into the food product and measuring an impedance of the food product between the at least two electrodes.

6. The method of claim 1, further comprising:
weighing the food product using a scale, resulting in a weight of the food product; and
identifying, via the processor, a food type of the food product based on the image and the weight, wherein the modifying of the purchase order is further based on the food type.

7. The method of claim 1, wherein the at least one internal property comprises one or more of protein content, fat content, seed content, water content, and degree of ripeness.

8. A system, comprising:
a processor; and
a non-transitory computer-readable storage medium having instructions stored which, when executed by the processor, cause the processor to perform operations comprising:
capturing an image of a food product;
analyzing an interior region of the food product via one or more analyzing devices;
based on the image and the analyzing of the interior region, generating a first dataset characterizing (i) at least one internal property of the food product, and (ii) an identity of the food product;
based at least on the first dataset, generating a second dataset characterizing a predicted quality of the food product and a recommended optimal time of receipt and quality of the food product by applying a regression analysis on at least the first dataset; and
modifying a purchase order for additional quantities of the food product based on the second dataset.

9. The system of claim 8, wherein the at least one internal property comprises an overall frequency response to ultra violet emission.

10. The system of claim 8, wherein the regression analysis further uses, as inputs, a time of receipt of the food product and a purchase time from the time of receipt.

11. The system of claim 8, wherein the one or more analyzing devices comprises an ultrasound device, and wherein the analyzing of the interior region via the ultrasound device generates an ultrasound.

12. The system of claim 8, wherein the one or more analyzing devices comprises a probe, the probe having at least two electrodes; and
wherein the analyzing of the interior region comprises inserting the probe into the food product and measuring an impedance of the food product between the at least two electrodes.

13. The system of claim 8, having additional instructions stored which, when executed by the processor, cause the processor to perform operations comprising:
weighing the food product using a scale, resulting in a weight of the food product; and
identifying a food type of the food product based on the image and the weight, wherein the modifying of the purchase order is further based on the food type.

14. The system of claim 8, wherein the at least one internal property comprises one or more of protein content, fat content, seed content, water content, and degree of ripeness.

15. A non-transitory computer-readable storage medium having instructions stored which, when executed by a processor, cause the processor to perform operations comprising:
capturing an image of a food product;
analyzing an interior region of the food product via one or more analyzing devices;
based on the image and the analyzing of the interior region, generating a first dataset characterizing (i) at least one internal property of the food product, and (ii) an identity of the food product;
based at least on the first dataset, generating a second dataset characterizing a predicted quality of the food product and a recommended optimal time of receipt and quality of the food product by applying a regression analysis on at least the first dataset; and
modifying a purchase order for additional quantities of the food product based on the second dataset.

16. The non-transitory computer-readable storage medium of claim 15, wherein the at least one internal property comprises an overall frequency response to ultra violet emission.

17. The non-transitory computer-readable storage medium of claim 15, wherein the regression analysis further uses, as inputs, a time of receipt of the food product and a purchase time from the time of receipt.

18. The non-transitory computer-readable storage medium of claim 15, wherein the one or more analyzing devices comprises an ultrasound device, and wherein the analyzing of the interior region via the ultrasound device generates an ultrasound.

19. The non-transitory computer-readable storage medium of claim 15, wherein the one or more analyzing devices comprises a probe, the probe having at least two electrodes; and
wherein the analyzing of the interior region comprises inserting the probe into the food product and measuring an impedance of the food product between the at least two electrodes.

20. The non-transitory computer-readable storage medium of claim 15, having additional instructions stored which, when executed by the processor, cause the processor to perform operations comprising:
weighing the food product using a scale, resulting in a weight of the food product; and
identifying a food type of the food product based on the image and the weight, wherein the modifying of the purchase order is further based on the food type.

* * * * *